United States Patent [19]

Chan

[11] Patent Number: 5,037,636

[45] Date of Patent: Aug. 6, 1991

[54] FLUORIDE STABILITY IN DICALCIUM PHOSPHATE DIHYDRATE COMPOSITION

[75] Inventor: Albert S. Chan, St. Louis, Mo.

[73] Assignee: Monsanto Chemical Company, St. Louis, Mo.

[21] Appl. No.: 425,093

[22] Filed: Oct. 23, 1989

[51] Int. Cl.$^5$ .......................... A61K 7/16; A61K 7/18
[52] U.S. Cl. ......................................... 424/52; 424/57
[58] Field of Search .................................... 424/52, 57

[56] References Cited

U.S. PATENT DOCUMENTS 3,105,798 10/1963 Holiday et al. ...................... 167/93
3,642,979 2/1972 Irani ...................................... 424/54
3,696,191 10/1972 Weeks ................................... 424/50

OTHER PUBLICATIONS

Cosmetic Science, vol. 1, Academic Press: New York, 1978, pp. 1-37; "Cosmetics and Dental Health", G. B. Winter, J. J. Murray, L. Shaw.

*Primary Examiner*—Shep K. Rose
*Attorney, Agent, or Firm*—Lawrence L. Limpus

[57] ABSTRACT

A dentifrice composition is disclosed which contains dicalcium phosphate dihydrate and other common ingredients and a zinc sodium tripolyphosphate compound.

17 Claims, No Drawings

FLUORIDE STABILITY IN DICALCIUM PHOSPHATE DIHYDRATE COMPOSITION

BACKGROUND OF THE INVENTION

This invention relates to a new dentifrice composition containing dicalcium phosphate dihydrate with an improved fluoride stability.

More particularly, this invention relates to a composition wherein small amounts of zinc salts are blended into dicalcium phosphate dihydrate powder to create a dicalcium phosphate dihydrate powder product which is more stable and which has a significantly higher fluoride stability.

More particularly, this invention relates to a dicalcium phosphate dihydrate based dentifrice which contains fluoride compounds wherein small amounts of a preferred zinc salt, zinc sodium tripolyphosphate salts, are blended into the dicalcium phosphate dihydrate powder to provide both a more stable dicalcium phosphate dihydrate and a significantly higher fluoride stability within the dentifrice.

DESCRIPTION OF THE PRIOR ART

From a cosmetic point of view, probably the most important aspect of dental health is the color and integrity of a person's teeth. Sparkling white teeth are generally considered aesthetically pleasing, whereas discolored, decayed, and broken down teeth are socially disadvantageous. While it has been found that adequate cleansing of the teeth can be achieved by the use of a tooth brush alone, most individuals require some abrasive to assist in removing materials that tend to accumulate on the teeth. The primary objective in using a dentifrice, or toothpaste, is to aid the cleansing of accessible tooth surfaces and to make tooth brushing more pleasant. The most important constituents of a toothpaste in relation to its mechanical cleansing properties are the abrasives and the surface active agents. For many years dicalcium phosphate dihydrate (DCPD) has been used as a dental polishing material.

In addition to the abrasives and surface active agents such as detergents, fluoride compounds have been added to toothpaste for a number of years. The cavity reducing effect of fluoride compounds in toothpaste is extremely well documented. The fluoride compound has most often been added to toothpaste in the form of sodium monofluorophosphate or stannous fluoride in an amount sufficient to yield 1000 ppm fluoride ion (ppmF.) in the toothpaste.

Dicalcium phosphate dihydrate (DCPD) is a dental polishing product which is mainly used in toothpaste containing sodium monofluorophosphate (MFP). Thus an important criterion is that the DCPD must be fairly compatible with the MFP. At this time about 1000 ppm of fluoride ion (1000 ppmF.) is included in fluoride containing toothpaste. The reaction of DCPD, and/or its components and derivatives, with the fluoride sources causes the formation of insoluble fluoride compounds such as calcium fluoride or fluoroapatite and a portion of the available fluoride is thus lost from the DCPD-based toothpastes. The amount of available fluoride that is lost depends upon the quality of the DCPD products; however, as much as one third of the available fluoride may be lost.

SUMMARY OF THE INVENTION

This invention is directed to a new composition of dicalcium phosphate dihydrate (DCPD) having improved DCPD stability and improved fluoride ion stability in DCPD-based toothpastes which contain fluoride compounds. Small amounts of inorganic zinc salts are blended into DCPD powder which is then used as the dental polishing product incorporated in toothpaste.

Zinc sodium tripolyphosphate, with any ratio of zinc to sodium, a preferred salt is blended into dicalcium phosphate dihydrate powder in a range of from about 0.4 percent to about 5.0 percent by weight of the dicalcium phosphate dihydrate, preferably in a range of from about 0.7 percent to about 3.7 percent by weight of the dicalcium phosphate dihydrate, and more preferably in a range of from about 1.2 percent to about 2.7 percent by weight of the dicalcium phosphate dihydrate powder.

In addition to the fluoride stability requirements, the DCPD, and the DCPD-based toothpaste which are produced, will have improved performance in additional tests such as the "Set Test" and the "Quick Fluoride Stability Test." While it has been found that the addition of a zinc sodium tripolyphosphate salt to the DCPD significantly improves the performance of the DCPD in the Set Test and the Quick Fluoride Stability Test, the addition of magnesium salts such as the preferred trimagnesium phosphate octahydrate (TMP) with a magnesium oxide (MgO) content in a range of from about 0.1 percent to about 0.6 percent by weight of the DCPD, and preferably in a range from about 0.3 percent to about 0.5 percent by weight, will also provide an improved performance of the DCPD, particularly in the Set Test. The addition of magnesium salts in combination with zinc sodium tripolyphosphate salts to the DCPD will synergistically improve the performance of the DCPD in the tests which are used to measure its performance as a component in toothpaste; however, the principal benefit is gained by adding the zinc sodium tripolyphosphate compounds to the DCPD.

DESCRIPTION OF THE PREFERRED EMBODIMENTS

Dicalcium phosphate dihydrate (DCPD) is a dental polishing product which is used in toothpaste or dentifrices. A DCPD-based dentifrice composition will contain DCPD as an abrasive or polishing agent, a source of fluoride ions, and any of the commonly used other ingredients of a dentifrice composition. The commonly used other ingredients of a dentifrice composition include flavoring substances such as esters and the oils of wintergreen, peppermint and spearmint and sudsing agents such as water-soluble alkyl and alkyl-ether sulfates and sulfonates having alkyl groups of from about 8 to 18 carbon atoms, water-soluble salts of sulfonated monoglycerides of fatty acids having from 10 to 18 carbon atoms, water-soluble salts of sulfated fatty alcohols having from 10 to 18 carbon atoms, salts of fatty acid esters of isethionic acid, and salts of fatty acid amides of taurines. They also include thickening agents such as water-soluble salts of cellulose ethers such as sodium carboxymethyl cellulose, natural gums and colloidal magnesium aluminum silicate or finely divided silica. Humectants which are used include glycerine, sorbitol and other polyhydric alcohols. If desired a suitable coloring agent may also be added to the dentifrice.

Fluoride compounds are added to a dentifrice or toothpaste at a level of about 1000 ppm of fluoride ion; however, during storage the fluoride ions react with other materials in the dentifrice, particularly the DCPD, to form insoluble fluoride compounds. Thus, as much as one third of the available fluoride, that is, the fluoride ions in the dentifrice which are available to provide protection against cavities, is lost before use. The addition of zinc tripolyphosphate compounds to the DCPD significantly improves the fluoride ion stability of the DCPD by reducing the formation of insoluble fluoride compounds. The reduction in the formation of insoluble fluoride compounds means that more fluoride ions remain in the dentifrice as reactive ions to prevent cavities in the teeth of the dentifrice user. In addition, the zinc tripolyphosphate salts improve the stability of the DCPD.

Two zinc tripolyphosphate compounds have been found to be highly effective in the improvement of the fluoride stability of dicalcium phosphate dihydrate (DCPD). Both compounds cause a significant increase in the fluoride ion stability in the presence of DCPD and both improve the stability of the DCPD in the Set Test which is one of the tests used to determine whether a specific batch of DCPD product meets the specifications for use as a polishing agent in a dentifrice. Two zinc tripolyphosphate compounds which have been found to be highly effective are $Zn_2NaP_3O_{10}\cdot 9H_2O$ and $ZnNa_3P_3O_{10}\cdot 12H_2O$, and a mixture of these two compounds. While the zinc sodium tripolyphosphates were found to significantly improve the fluoride ion stability and the Set Test performance of the DCPD, it is also possible to use other zinc salts such as zinc chloride, zinc oxide, zinc orthophosphate, zinc pyrophosphate, zinc sulfate heptahydrate, and zinc trimetaphosphate. However, these other zinc salts are less effective than the zinc tripolyphosphate compounds.

The preferred zinc sodium tripolyphosphate salts may be prepared according to the following reactions:

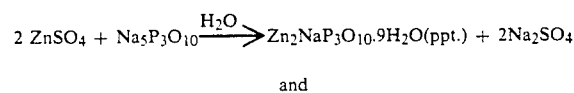

and

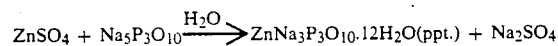

The second of these materials, $ZnNa_3P_3O_{10}\cdot 12H_2O$, is about 20 times more soluble than the first, $Zn_2NaP_3O_{10}\cdot 9H_2O$. Therefore, for the stabilization of DCPD, the $Zn_2NaP_3O_{10}\cdot 9H_2O$ is a better choice because the lower solubility of the zinc compound will have less thickening effect on the final DCPD based toothpaste. This may be further explained by noting that polyphosphate anions have a thickening effect on DCPD/glycerin slurries. When a soluble polyphosphate compound such as zinc sodium tripolyphosphate ($ZnNa_3P_3O_{10}\cdot 12H_2O$), tetrasodium pyrophosphate (TSPP), or sodium tripolyphosphate (STP) was mixed into a slurry containing a 1:1 ratio by weight (1:1, Wt/Wt) of DCPD/87.5% glycerin solution and the final mixture was allowed to stand at ambient temperature for one day, the DCPD was found to settle at the bottom and it became thick and hard. This hardening effect was not found for a similar mixture of DCPD/87.5 % glycerin when the zinc sodium tripolyphosphate $Zn_2NaP_3O_{10}\cdot 9H_2O$ was mixed with the DCPD. This effect was believed to be caused by the substantially lower solubility of the $Zn_2NaP_3O_{10}\cdot 9H_2O$.

The effectiveness of the zinc sodium tripolyphosphates in the stabilization of DCPD to prevent dehydration of the DCPD and to prevent the formation of insoluble fluoride compounds is probably due to its double protecting effect. Both the zinc cations and the tripolyphosphate anions contribute to the stabilization effect when they are mixed into DCPD. An advantage from the use of zinc tripolyphosphates as the tripolyphosphate source is that the pH of the slurries that are created is close to neutral. This is important for the fluoride stabilization of DCPD because both acidic and alkaline conditions can induce the decomposition of DCPD and of sodium monofluorophosphate (MFP). Also, oral products desirably have a neutral pH.

Another advantage found when using zinc tripolyphosphate compounds in the fluoride stabilization of DCPD is that they are only marginally soluble. While the small amounts of zinc cations and tripolyphosphate anions released from these compounds provide greatly enhanced fluoride stability for DCPD, the low solubility of these compounds prevents the total capturing of the free calcium ions from the DCPD by the tripolyphosphate ions. Therefore, the zinc sodium tripolyphosphate compounds may be visualized as slow releasing sources of zinc and tripolyphosphate ions for the long term stabilization of the DCPD.

Historically, DCPD products have been stabilized by magnesium salts, such as trimagnesium phosphate (TMP), dimagnesium phosphate (DMP), and magnesium pyrophosphate. Although the exact nature of the stabilization is not known, there are speculations that the effects of the magnesium and pyrophosphate salts are caused by the absorption of the magnesium ions or pyrophosphate anions at the crystal surface of DCPD so that they protect the DCPD from dehydration or disproportionation. While the fluoride stability of DCPD is substantially enhanced by the addition of zinc sodium tripolyphosphate compounds, the improvement in fluoride stability may be increased even more if the zinc sodium tripolyphosphate compounds are used in combination with a magnesium salt such as (TMP) instead of as a replacement for the magnesium salts.

The invention will be better understood by the following examples which illustrate, but do not limit, the preparation and effectiveness of compositions of this invention. In the following examples, the amount of soluble fluoride ions remaining in the formulations was measured after acceleration aging tests which were equivalent to storage at ambient temperature for about two years. Two accelerated aging tests were used. The first requires storage of the product at 60° C. for five days and the second requires storage at 49° C. (120° F.) for 21 days.

EXAMPLE 1

Zinc sodium tripolyphosphate, $Zn_2NaP_3O_{10}\cdot 9H_2O$, (ZSTP) was produced for use in the following examples. It was produced by dissolving 1052 grams of $ZnSO_4\cdot 7H_2O$ (3.66 moles) in three liters of water at ambient temperature. A second solution was produced by dissolving 613 grams of sodium tripolyphosphate (STP) (1.67 moles) in five liters of water. The STP solution was added to the zinc sulphate solution while the solution was being mechanically stirred and the stirring was continued for two hours after all of the STP solution was added. The white precipitate was filtered, washed thoroughly with eight liters of water, and then filtered again. The wet cake was dried at 50° C. and de-agglomerated to obtain 926 grams of white powder.

The composition of the powder determined by an elemental analysis was Zn-23.8%, Na-4.04%, and $P_2O_5$-38.1% which was compared to the theoretical analysis of Zn-23%, Na-4%, and $P_2O_5$-37.4% and an x-ray powder diffraction study to confirm that the white powder was $Zn_2NaP_3O_{10} \cdot 9H_2O$ (ZSTP).

EXAMPLE 2

A control dentifrice or toothpaste, Sample 2A, was produced by blending 98.7 grams of DCPD with 90.6 grams of 87.5% glycerin containing 0.6% tetrasodium pyrophosphate (TSPP), 7.72 grams of 20% sodium monofluorophosphate (MFP), and 2.98 grams of sodium lauryl sulphate (SLS). This formulation contains about 1000 ppm soluble fluoride ions (1000 ppmF.). Additional samples of the dentifrice or toothpaste, Samples 2B–2F, were prepared by dry blending zinc sodium tripolyphosphate (ZSTP) from Example 1 with DCPD. Various amounts of ZSTP were added to the DCPD to provide a total sample weight of 98.7 grams which was then formulated with the other ingredients as described above. The resulting pastes were subjected to the accelerated aging tests described above. The amount of soluble fluoride ions (ppmF.) remaining in the paste were measured. The measured results are shown in Table 1.

TABLE 1

| Example No. | DCPD (grams) | ZSTP (grams) | Test 1 60° C. - 5 days (ppm F.) | Test 2 49° C. - 21 days (ppm F.) |
| --- | --- | --- | --- | --- |
| 2-A | 98.7 | 0 | 788 | 749 |
| B | 98.0 | 0.7 | 833 | 796 |
| C | 97.3 | 1.4 | 854 | 827 |
| D | 96.6 | 2.1 | 863 | 824 |
| E | 95.2 | 3.5 | 858 | 844 |
| F | 98.3 | 0.4 | 806 | 792 |

Another indication of the fluoride stability of DCPD products is shown by the Quick Fluoride Stability Test which provides a measurement of the soluble fluoride available in the DCPD-based dentifrice. For the Quick Fluoride Stability Test, a solution was prepared by mixing 1000 grams of deionized water with 1000 grams of glycerin and with a measured amount of sodium monofluorophosphate ($Na_2PO_3F$) to create a solution with about 2000 ppmF. A weighed portion of the DCPD sample to be tested was mixed into the solution to produce a slurry. The slurry was placed in a bottle, heated in a boiling water bath for one hour, cooled, and centrifuged. After centrifuging the liquid layer was acid hydrolyzed with HCl and then analyzed with a fluoride-specific ion electrode to determine the amount of free fluoride ion remaining. The fluoride ion loss is attributed to the formation of insoluble fluoride compounds by reaction with the DCPD.

EXAMPLE 3

A sample of approximately 150 grams of DCPD was divided into six portions, A-F. Trimagnesium phosphate (TMP) and zinc sodium tripolyphosphate, $Zn_2NaP_3O_{10} \cdot 9H_2O$, (ZSTP) prepared as described in Example 1 were added as indicated in Table 2 below to show the substantial improvements in fluoride stability that may be achieved by the addition of these two compounds to the DCPD. The DCPD blends were added to the fluoride containing solution which was prepared, as described above, for the Quick Fluoride Stability Test. The available fluoride in each solution was measured using the Quick Fluoride Stability Test and the results of these measurements are shown in Table 2.

EXAMPLE 4

The experiment of Example 3 was repeated with a different sample of DCPD. The DCPD material was divided into 23.7 gram portions and one 24.0 gram portion which was utilized as the control. The remaining portions were blended by the addition of ZSTP and TMP as described below in Table 2. Each blend was added to the fluoride containing solution which was prepared as described above and the fluoride stability was measured using the Quick Fluoride Stability Test. The amount of available fluoride ions that were measured is shown in Table 2.

TABLE 2

| Example/ Sample No. | DCPD (grams) | ZSTP (grams) | TMP (grams) | Fluoride (ppm F.) |
| --- | --- | --- | --- | --- |
| 3-A | 24 | 0 | 0 | 746 |
| B | 23.7 | 0 | 0.3 | 820 |
| C | 23.7 | 0.3 | 0 | 926 |
| D | 23.4 | 0.3 | 0.3 | 1099 |
| E | 23.1 | 0.6 | 0.3 | 1451 |
| F | 23.4 | 0 | 0.6 | 781 |
| 4-A | 24.0 | 0 | 0 | 694 |
| B | 23.7 | 0 | 0.3 | 780 |
| C | 23.7 | 0.3 | 0 | 867 |
| D | 23.4 | 0.3 | 0.3 | 967 |

Example 3 and Example 4 show the significant improvement in the fluoride stability of DCPD when small amounts of zinc sodium tripolyphosphate are blended into the DCPD. The Examples further show that trimagnesium phosphate (TMP) also improves the fluoride stability of the DCPD; however, to a lesser extent than the improvement shown by the addition of the zinc sodium tripolyphosphate. It is recognized, however, that a blend of DCPD with both zinc sodium tripolyphosphate and trimagnesium phosphate exhibits a greater fluoride stability than a blend of DCPD with either of the additives alone and that the combination of zinc sodium tripolyphosphate and trimagnesium phosphate exhibits a greater than additive effect, that is, a synergistic effect, on the fluoride stability.

Another test performed to determine the quality of the DCPD is the hydraulic stability test which is generally known as the Set Test. The Set Test requires the heating of a slurry of an amount of DCPD product in an equal amount, by weight, of 87.5% glycerin at 100° C. for 30 minutes. The test requires both a minimum change in the texture of the slurry and that no grits are formed in the slurry after the high temperature treatment. The main cause for poor Set Test performance for DCPD products is the dehydration of the DCPD (dicalcium phosphate dihydrate) to DCPA (dicalcium phosphate, anhydrous). The change in the texture of the slurry and the formation of grits becomes obvious when a certain level of dehydration takes place. The grits have been determined to be solely DCPA.

Soluble magnesium salts such as magnesium chloride and magnesium perchlorate can suppress the dehydration of DCPD and can thus improve the Set Test performance of the DCPD. However, most soluble magnesium salts are hygroscopic and they may, therefore, create some caking problems when blended into the DCPD product. Furthermore, the presence of excess soluble magnesium salts lowers the fluoride stability in the DCPD product because the magnesium ions react readily with fluoride ions to form insoluble magnesium fluoride.

It has been known that insoluble magnesium salts such trimagnesium phosphate octahydrate (TMP) and dimagnesium phosphate trihydrate (DMP) can suppress the dehydration of DCPD and improve the performance of the DCPD in the Set Test. TMP is superior to DMP in the suppression of the dehydration of DCPD and it is, therefore, the first choice for use as a stabilizer of DCPD for the Set Test. However, the fluoride stability in the DCPD deteriorates when the MgO content of the DCPD reaches a level above about 0.6%.

Inorganic compounds other than magnesium salts have also been studied. Among the various compounds tested, zinc sodium tripolyphosphates were the best for the stabilization of DCPD. The addition of zinc sodium tripolyphosphates to the DCPD product improved the Set Test performance and, in addition, increased the fluoride stability of the DCPD product substantially.

EXAMPLE 5

A control for the Set Test was prepared by mixing 30 grams of a DCPD sample with 30 grams of an 87.5% glycerin solution to make a smooth slurry. About one-half of the slurry was placed in a test tube which was then lightly stoppered and placed in a water bath at 100° C. for 30 minutes. Following the heating, the slurry within the test tube was allowed to cool to ambient temperature by standing at ambient temperature for about two hours. The cooled slurry was stirred slightly with a stirring rod and the texture of the slurry was noted. A small portion of the cooled slurry, for example, 1 gram or less, was placed on a glass slide which was then tilted at an angle of about 60° to allow the cooled slurry to flow. When the flow of the slurry reached the bottom edge of the slide, the slide was placed on a flat surface. The grit formation, if any, and the flow property of the cooled slurry were observed. The slurry was thicker and drier and a lot of large grits were formed.

EXAMPLE 6

The procedure of Example 5 was repeated. A dry blend of 29.7 grams of DCPD and 0.3 grams of zinc sodium tripolyphosphate, $Zn_2NaP_3O_{10}.9H_2O$, was prepared and a slurry was produced by mixing the blend with 30 grams of an 87.5% glycerin solution. After heating and cooling the slurry, a small amount was placed upon a glass slide and observed as set out in Example 5. The cooled slurry had a good texture and there were no grits formed. This result demonstrates that the addition of zinc sodium tripolyphosphate to DCPD can improve the Set Test performance of the DCPD.

The foregoing description of this invention is not intended as limiting the invention. As will be apparent to those skilled in the art, many variations on and modifications to the embodiments described above may be made without departure from the spirit and scope of this invention.

I claim:

1. A dentifrice composition comprising dicalcium phosphate dihydrate containing from about 0.4% to about 5.0%, by weight of said dicalcium phosphate dihydrate, of a zinc sodium tripolyphosphate compound, a source of fluoride ions and other common ingredients employed in a dentifrice composition.

2. The dentifrice composition of claim 1 wherein said zinc sodium tripolyphosate compound is $Zn_2NaP_3O_{10}.9H_2O$.

3. The dentifrice composition of claim 2 wherein said dicalcium phosphate dihydrate contains from about 0.7% to about 3.7%, by weight of said dicalcium phosphate dihydrate, of said zinc sodium tripolyphosphate compound.

4. The dentifrice composition of claim 3 wherein said dicalcium phosphate dihydrate contains trimagnesium phosphate octahydrate which provides from about 0.1% to about 0.6% by weight magnesium oxide in the dicalcium phosphate dihydrate.

5. The dentifrice composition of claim 4 wherein said dicalcium phosphate dihydrate contains trimagnesium phosphate octahydrate which provides from about 0.3% to about 0.5% by weight magnesium oxide in the dicalcium phosphate dihydrate.

6. The dentifrice composition of claim 3 wherein said dicalcium phosphate dihydrate contains from about 1.2% to about 2.7%, by weight of said dicalcium phosphate dihydrate, of said zinc sodium tripolyphosphate compound.

7. The dentifrice composition of claim 6 wherein said dicalcium phosphate dihydrate contains trimagnesium phosphate octahydrate which provides from about 0.3% to about 0.5% by weight magnesium oxide in the dicalcium phosphate dihydrate.

8. The dentifrice composition of claim 1 wherein said zinc sodium tripolyphosphate compound is $ZnNa_3P_3O_{10}.12H_2O$.

9. A dental polishing product comprising dicalcium phosphate dihydrate containing from about 0.4% to about 5.0%, by weight of said dicalcium phosphate dihydrate, of a zinc sodium tripolyphosphate compound.

10. The dental polishing product of claim 9 wherein said zinc sodium tripolyphosphate compound is $Zn_2NaP_3O_{10}.9H_2O$.

11. The dental polishing product of claim 10 wherein said dicalcium phosphate dihydrate contains from about 0.7% to about 3.7%, by weight of said dicalcium phosphate dihydrate, of said zinc sodium tripolyphosphate compound.

12. The dental polishing product of claim 11 wherein said dicalcium phosphate dihydrate contains trimagnesium phosphate octahydrate which provides from about 0.1% to about 0.6% by weight magnesium oxide in the dicalcium phosphate dihydrate.

13. The dental polishing product of claim 12 wherein said dicalcium phosphate dihydrate contains trimagnesium phosphate octahydrate which provides from about 0.3% to about 0.5% by weight magnesium oxide in the dicalcium phosphate dihydrate.

14. The dental polishing product of claim 11 wherein said dicalcium phosphate dihydrate contains from about 1.2% to about 2.7%, by weight of said dicalcium phosphate dihydrate, of said zinc sodium tripolyphosphate compound.

15. The dental polishing product of claim 14 wherein said dicalcium phosphate dihydrate contains trimagnesium phosphate octahydrate which provides from about 0.3% to about 0.5% by weight magnesium oxide in the dicalcium phosphate dihydrate.

16. The dental polishing product of claim 9 wherein said zinc sodium tripolyphosphate compound is ZnNa$_3$P$_3$O$_{10}$.12H$_2$O.

17. A composition for improving the fluoride stability of a fluoride-containing dentifrice comprising dicalcium phosphate dihydrate containing from about 0.4% to about 3.7% Zn$_2$NaP$_3$O$_{10}$.9H$_2$O, by weight of said dicalcium phosphate dihydrate, and trimagnesium phosphate octahydrate which provides from about 0.3% to about 0.5% by weight magnesium oxide in the dicalcium phosphate dihydrate.

* * * * *

Disclaimer 5,037,636—*Albert S. Chan*, St. Louis, Mo. FLUORIDE STABILITY IN DICALCIUM PHOSPHATE DIHYDRATE COMPOSITION. Patent dated Aug. 6, 1991. Disclaimer filed April 22, 1991, by the assignee, Monsanto Chemical Co.

The term of this patent subsequent to July 16, 2008, has been disclaimed.